United States Patent [19]

Bouchier et al.

[11] Patent Number: 4,839,492
[45] Date of Patent: Jun. 13, 1989

[54] PLASMA SCALPEL

[76] Inventors: Guy Bouchier, 106 rue Jean-Jaurès, Saint Laurent, 77440 Lizy sur Ourcq; Francois Lhuisset, Pavillon 19, 14ter rue des Vallées, 91800 Brunoy, both of France

[21] Appl. No.: 157,222

[22] Filed: Feb. 18, 1988

[30] Foreign Application Priority Data

Feb. 19, 1987 [FR] France .................. 87 02197

[51] Int. Cl.$^4$ ........................... B23K 9/00
[52] U.S. Cl. .............. 219/121.48; 219/121.52; 219/121.57; 219/121.39
[58] Field of Search .......... 219/121 PR, 121 PS, 219/121 PC, 75, 74, 121 PL, 121 PK, 121 PA, 121 PY, 121 P, 121 PT, 121 PW

[56] References Cited

U.S. PATENT DOCUMENTS

| | | |
|---|---|---|
| 2,923,811 | 2/1960 | Feldmeyer et al. .......... 219/121 PS |
| 3,312,566 | 4/1967 | Winzeler et al. .............. 219/121 PS |
| 3,358,114 | 12/1967 | Inoue ................ 219/121 PS |
| 3,604,889 | 9/1971 | Rohrberg ................ 219/121 PS |
| 4,136,273 | 1/1979 | Fujita et al. ................ 219/121 PR |
| 4,147,957 | 4/1979 | Hildebrand ............ 219/121 PR |
| 4,275,287 | 6/1981 | Hiratake .............. 219/121 PA |
| 4,495,399 | 1/1985 | Cann ................ 219/121 PQ |

*Primary Examiner*—M. H. Paschall
*Attorney, Agent, or Firm*—Sughrue, Mion, Zinn, Macpeak and Seas

[57] ABSTRACT

In a device of the plasma scalpel type (40, 41) including at least two spaced-apart electrodes (21, 22) subjected to electrical potential differences such that electric arcs take place therebetween, together with structures for producing at least one fluid flow passing through a region of space where said electric arcs occur, the potential differences being alternating potential differences at medium or high frequency, the ends of said electrodes are substantially filiform and forming an angle therebetween which is preferably acute, and a voltage step-up transformer is incorporated therein in order to deliver the alternating potential differences, with the fluid flows arriving from within the angle or along at least one of said electrodes. In one embodiment, each of the electrodes is constituted by a wire of electrically conductive material (21, 22) and is placed inside an electrode-carrier duct (27, 28) whose inside diameter is slightly greater than the diameter of the electrode, with the end of the electrode projecting beyond the duct and with the fluids being conveyed along said electrode-carriers. The device is versatile. It has numerous applications, in particular in dental surgery, but also for operations of etching, cutting out, welding, or recharging with material, treatments to composite materials, etc.

11 Claims, 2 Drawing Sheets

PLASMA SCALPEL

The present invention relates to a method of cutting and/or treating hard or soft substances, in particular living tissue, by producing a flow of ionized gas (or plasma) in the vicinity of, or at the surface of, or inside said substances or said tissue. The invention also relates to a device, called a plasma scalpel or a micro-blowtorch, for implementing the method.

BACKGROUND OF THE INVENTION

The principle of cutting or working on substances by producing a plasma (or highly ionized gas) is not novel per se. Plasma may be created by passing a gas through an electric arc. The electrical energy in the arc is converted into thermal energy in the gas, after passing through the electric arc the gas appears in the form of a partially ionized plasma at high temperature. In medicine, experimental plasma scalpel prototypes have been made using two coaxial electrodes, with an outer anode forming a nozzle and an inner cathode terminating at a point which is set back slightly from the end of the outer anode. A flow of gas running along the inside space thus provided between the outer electrode and the inner electrode passes through the electric arc produced at the ends of the electrodes and leaves in the form of a high temperature plasma. This disposition is shown in the diagram of FIG. 1 where the nozzle-shaped outer anode 1 and needle-shaped inner cathode 2 can be seen. A degree of electric arcing is symbolized by dashed lines 3, and a flow of gas by arrows 4, together with plasma output 5. A prototype plasma scalpel of this type was developed by Link et al at the University of Purdue in 1970. The high temperature plasma jet coming from the nozzle of this prototype plasma scalpel is generated by passing argon through a D.C. electric arc. The electric arc is struck by putting the two electrodes into contact. The average plasma temperature at the outlet from the nozzle is approximately 3,000° C.

This prior art device nevertheless suffers from several drawbacks. While plasma is being produced, the anode reaches very high temperatures and requires considerable cooling, while the cathode does not require so much cooling. The use of a system which propels the arc by means of a jet of gas well beyond the electrodes spreads out the volume occupied by the phenomenon, thereby making it impossible to reach very high temperatures; cooling due to the effect of the gas expanding together with the very fast natural cooling of the plasma where no longer excited appear to be the causes of this phenomenon. The use of a rare gas is becoming less and less common since rare gases are expensive and have a poorer heat transfer coefficient.

Preferred implementations of the present invention provide a device and a method of cutting or treating hard to soft substances, and in particular living tissue, which method and device are different in design from the prior art methods and devices in this field, in particular for obtaining greater safety in use and very accurate localization, together with a degree of versatility. The invention is essentially concerned with a tool or instrument that can be operated by hand, and preferably with one hand only.

SUMMARY OF THE INVENTION

According to the present invention a device of the plasma scalpel type comprises at least two spaced-apart electrodes subjected to different electrical potentials such that electric arcing occurs therebetween, and means for producing one or more fluid flows passing through a region of space where said electric arcing takes place. For medical or dental use, said potential differences must necessarily be without risk of electrocution, i.e. at medium or high frequency, for example. The ends of said electrodes are substantially filiform or pointed and they preferably form an acute angle with each other. Advantageously, said fluid flows are directed from the inside of said angle towards its outside, or else along said electrodes.

The device may comprise only two electrodes in conjunction with a single phase feed giving rise to an alternating plasma. It may also include more than two electrodes with a polyphase feed: for example, if three or six electrodes are used, the electrodes may be fed with three-phase electricity.

Advantageously, the ends of the electrodes (or the electrodes themselves) are elongate in shape, or are of small cross-section, so as to enhance a point effect which tends to orient the ends of the electric arc into alignment with the ends of the electrodes. To this end, the electrodes may be in the form of wires.

The fluid flow serves several functions: it directs the plasma jet; and it cools the electrodes and/or the substance during operation of the device. It may also participate in the formation of the plasma.

The purpose of such a device is thus to produce a plasma in a small volume by an electric discharge which is directed by the point effect and/or by fluid displacement in order to be applied against the surface of said substances or said tissues, thereby digging into them, cutting them up, or more generally treating them by heating them rapidly to a very high temperature. When cutting living tissue with such a device, operating temperatures are generally high so that the operation takes place very quickly, i.e. in passes occupying a fraction of a second so that the tissue does not have time to become heated in depth. As a result, when dealing with living tissue, pain is reduced since the thermal effect is very superficial and subsequent scarring of the tissue takes place quickly, as has been shown on tests performed in the laboratory on rats and rabbits. In other words, since the thermal gradient is very steep, and since the application time can be very short, the zone which is thermally affected (the coagulated zone with living tissue) is very small, thereby explaining the good results obtained.

The electrodes project far enough from their electrode carriers to have their tips at a short distance from one another and in contact or nearly in contact with the zone to be treated, which gives rise to an exceptional temperature gradient that is most suitable for reducing the affected thermal zone. It is possible to work while pressing against the surface to be treated, and this is essential for reasons of accuracy when the instrument is manually guided. Such details are very important, for example in surgery when melting hard tissue or volatilizing soft tissue; in such cases it is essential to use an alternating current at a frequency which is high enough to be innocuous for living beings and/or a voltageboosting system which is fairly small, with its size for given power being related to the frequency used.

BRIEF DESCRIPTION OF THE DRAWINGS

Embodiments of the invention are described by way of example with reference to the accompanying drawings, in which.

MORE DETAILED DESCRIPTION

Figure 1:
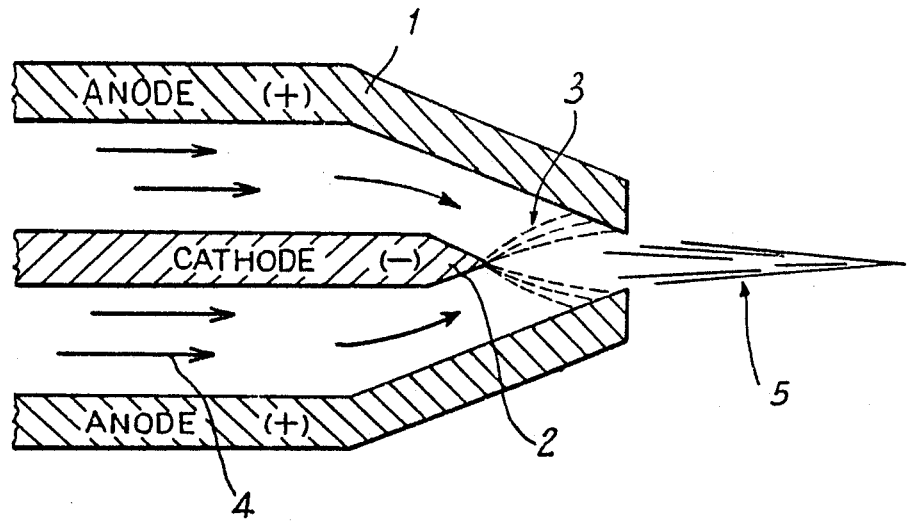
FIG. 1 is a diagrammatic section through a prior art plasma scalpel.
Figure 2:
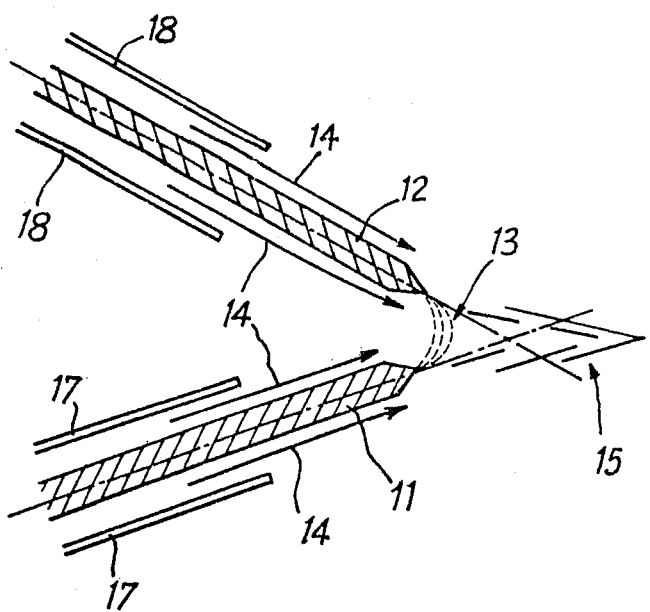
FIG. 2 is a diagrammatic section through a plasma scalpel in accordance with the invention.

FIG. 1 has already been described as illustrating the prior art. FIG. 2 is similar to FIG. 1, but relates to a plasma scalpel in accordance with the invention. In this figure, two substantially linear electrodes which are pointed at their ends 11 and 12 preferably form an acute angle and are disposed relative to one another and are subjected to alternating electrical potential differences in such a manner as to cause electric arcing 13 to take place between their ends. A flow of fluid arrives along the electrodes 11 and 12 via respective ducts 17 and 18 surrounding the electrodes and is applied to the electric arc as shown by arrows 14. This produces a jet of plasma 15 substantially along the bisector of the longitudinal axes of the electrodes 11 and 12.

The ducts 17 and 18 can thus serve as electrode carriers, and may be at the same potentials as the electrodes. The FIG. 2 disposition is advantageous since the fluid passing along the ducts 17 and 18 can serve not only for producing the plasma jet, but also for cooling the electrodes. In a variant, each electrode-carrier may be surrounded by a sheath suitable for conveying fluid in a space provided between said sheath and the electrode-carrier, thereby reducing play between each electrode and its electrode-carrier.

The disposition of the electrodes and the substantially linear (i.e. small cross-section relative to length) or pointed shape of their ends enhances the "point effect" phenomenon whereby the electric arc does not extend along a straight line between the tips of the electrodes, but tends to leave each electrode tip along the longitudinal axis thereof.

Further, the fluid flow tends to blow the arc downstream which also enhances the curvature of the electric arc into the operating field.

Unlike prior art devices, the plasma scalpel in accordance with the invention is fed with A.C., which as the advantage of causing symmetrical wear to the electrodes unlike the pitting and sharpening effects of an electric arc between electrodes which are fed with D.C. In addition, heat is evenly distributed between the electrodes. The preferred use of a high (or medium) frequency enhances remote excitation of the fluids used, and also enhances heating of the surface against which the electrodes are applied by the Joule effect and/or by dielectric losses, depending on the substances being treated, with all of these phenomena co-operating to keep electrode wear down to a minimum together with cooling thereof which is preferably coaxial.

Each electrode may be constituted, for example, by a wire of a metal which withstands very high temperatures well, for example tungsten, or any other sufficiently conductive substance, which may be refractory and relatively immune to high temperature attack in the fluid(s) used. The use of filiform electrodes means that it is preferable to apply low electric currents at high voltage.

In accordance with the invention, the device is fed with electric current which is adjustable and/or regulated. The voltage at the terminals of the electrodes must be adapted as a function of the length of the electric arc, and since the arc is deformed somewhat outwardly by the flow of fluid, this length may vary. Further, the electric arc may be triggered in conventional manner by moving the electrodes closer together, or else by increasing the voltage between the electrode terminals, or by applying current which is amplitude modulated. In addition, the different natures of the substances that are treated, in particular with respect to their surface conductivities and their dielectric properties, cause such adjustments to vary. Regulation makes the device easier to use.

The fluid may be a gas, in particular air or a rare gas, but it may also be any other suitable fluid. Further, it may be desirable to use several different fluids.

Figure 3:
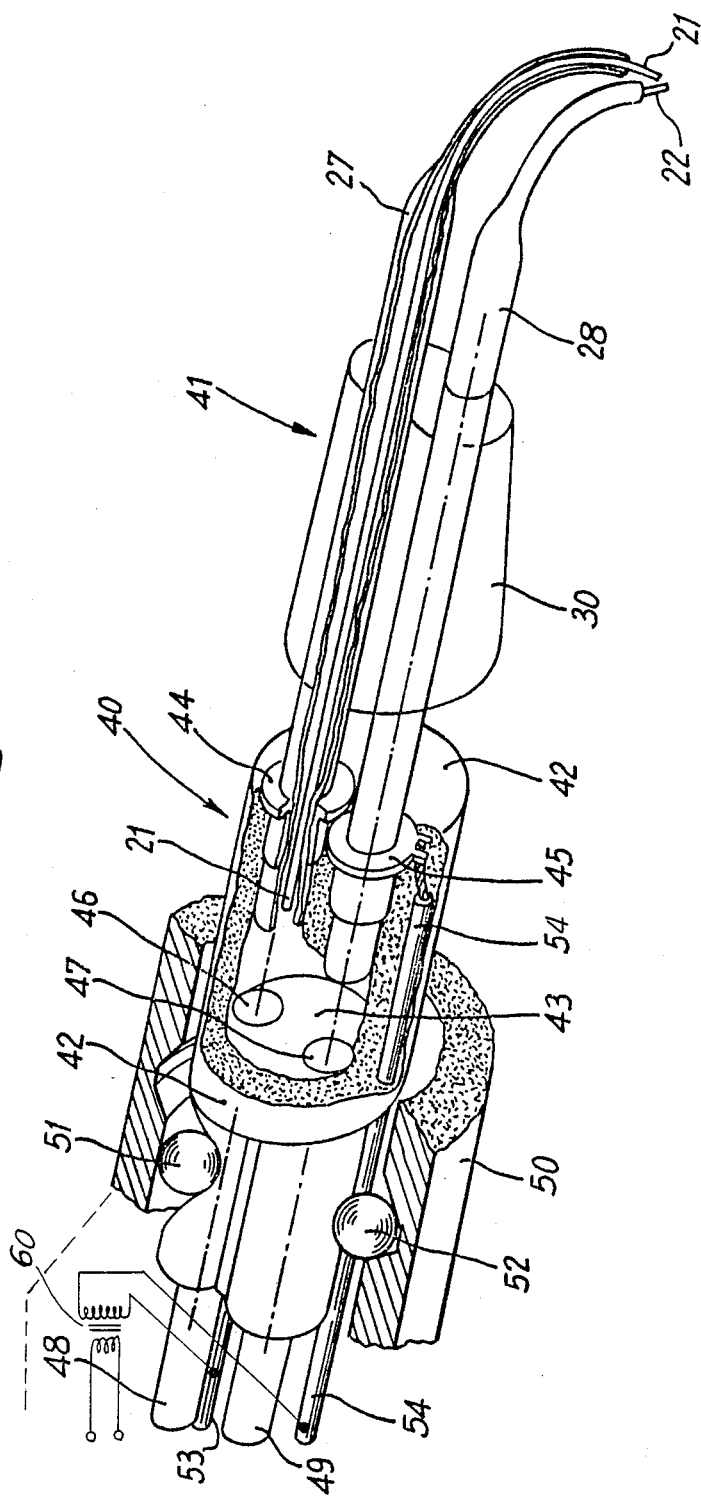
FIG. 3 is a partially exploded view of a plasma scalpel in accordance with a particular embodiment of the invention.

In FIG. 3, a plasma scalpel in accordance with the invention comprises a tool carrier 40 and an electrode-carrier assembly 41. The electrode-carrier assembly 41 is mainly constituted by two cylindrical electrode-carrier ducts 27 and 28 each of which terminates by a rounded or bent front portion of smaller diameter. An electrode 21 or 22 is placed in each of the ducts 27 or 28 and is in the form of a tungsten wire whose diameter is slightly less than the diameter of said rounded duct portion. Advantageously, both electrode-carrier ducts 27 and 28 have their middle portions received in an insulating sleeve 30.

The tool carrier 40 comprises a sealed housing 42 having a chamber 43 therein and having two openings in its front wall provided with respective sockets 44 and 45 which define two cylindrical passages between said chamber 43 and the outside passing through the sealed housing 42, with the diameters of the sockets being substantially the same as the outside diameters of the two electrode-carrying ducts 27 and 28. In the "rear" wall of the sealed housing 42 opposite to its front wall, there are two openings 46 and 47 into which two tubes 48 and 49 open out, i.e. one tube per opening. Closure means (which in the example shown in FIG. 3 are of the type comprising balls 51 and 52 and a slidable control ring 50) are provided immediately upstream from the openings 46 and 47 in order to allow or prevent the fluids contained under pressure in the tubes 48 and 49 passing into the chamber 43.

In a particularly advantageous embodiment of the invention, the closure means may comprise a rigid sleeve having at least two fluid admission tubes which are highly deformable inside the sleeve so that a high pressure in one of the tubes closes the other tube(s) by compression against the inside walls of said rigid sleeve. In this embodiment there is no need for a manual fluid control means on the instrument itself; a pedal-operated control is capable of putting each selected tube under pressure.

The electrode-carrier ducts 27 and 28 are inserted into respective ones of said sockets 44 and 45. When a fluid under pressure is to be found in the chamber 43, it flows along the electrode-carrier ducts 27 and 28 around the electrodes 21 and 22.

Said conductive sockets 44 and 45 are connected, e.g. by soldering or crimping, to respective insulated conductors 53 and 54 which, in the FIG. 3 example, are embedded in the wall thickness of the sealed housing 42 to project from the rear wall thereof and are then connected to a current generator via a voltage-boosting transformer (neither of which is shown in the figure). The sockets 44 and 45 and said electrode-carrier ducts 27 and 28 are made from an electrically conductive material. Since each socket 44 and 45 is, by construction, in contact with the electrode-carrier duct inserted therein (i.e. ducts 27 and 28 respectively), and since each electrode 21 and 22 respectively is in contact with its own electrode-carrier duct, a potential difference between the insulated conductors 53 and 54 is transmitted to the electrodes 21 and 22. Further, the tube 48 is put under air pressure. It is not essential for the other tube 49 to be used since it is not required in order to enable the invention to operate. However, it constitutes an advantageous variant of the invention making it possible to pass a fluid other than air into the electrode-carrier ducts, where necessary.

In a variant, said closure means may be omitted and a fluid (air in this case) may flow along the electrodes on a permanent basis.

A device in accordance with the invention preferably includes means (not shown), in particular water-jet means, associated therewith for bringing water into the vicinity of the ends of the electrodes. The water may be conveyed along at least one of the electrode-carrier ducts.

The electrode-carriers may also be elliptical or polygonal in section, etc., since any shape that allows it to perform its function is satisfactory, and the wire may optionally be worked in order to enhance friction or stiffness, for example it may be undulating in shape, or provided with a rib, etc. Since the filiform electrodes are smaller in diameter than the electrode-carriers, the electrodes may be retained by friction due to internal geometrical irregularities inside the electrode-carriers, e.g. curves. Such retention may also be obtained by external irregularities of the filiform electrodes, for example undulations therein.

This head-forming electrode-carrier assembly may optionally be removable, interchangable, or single-purpose. More generally, the electrode-carrier ducts and/or said electrodes may be consumable, interchangable, and replaceable. The electrode-carriers 27 and 28 may be rectilinear and convergent for some applications, but for dental applications it is advantageous to use a "counter-angle" or right angle shape in order to improve ease of use. The instrument shape shown in FIG. 3 makes observation from above possible while the instrument is being used, and this is not possible with rotary dental instruments. In general, and preferably, the two electrodes form plane curves each defining a plane, with said planes being at an angle to one another such that the operating field can be observed from inside said preferably acute angle in order to enable said observation to take place along an axis which is substantially perpendicular to the surface of the object on which work is taking place.

The electrode-carrier assembly may be readily interchangable, for example simply by friction, for the purpose of electrode replacement, or for changing the configuration of the terminal portion of the instrument, or for asepsis, with asepsis being an important reason in medical applications.

In accordance with the present invention, a method of cutting and treating hard or soft substances, in particular living tissue, using the device shown in FIG. 3, comprises the following steps:

if necessary, a small quantity of water is applied to the output from the electrode-carriers in order to improve the conductivity of the space between the electrodes and thus facilitate striking an arc therebetween;

the air feed is switched on to put chamber 43 under air pressure, thereby causing air to flow along and around the electrode;

high frequency current is switched on to strike the electric arc, said current being optionally frequency or amplitude modulated and being provided by the generator;

where applicable, the modulation of the electric current is adapted to match the work to be performed; and a high frequency working current is applied for application periods lasting a fraction of a second to a few seconds.

The last-mentioned step means that work takes place for periods of time occupying a fraction of a second to a few seconds and interspersed with periods of relaxation which may be used for cooling the substance being worked on, e.g. by water, spray, or other means.

Means may be provided for adjusting the differences in electrical potential, and the relaxation periods between the periods during which said potential differences are applied, and also for adjusting the durations of said application periods and the instance at which the, or each, fluid is applied.

The current generator is advantageously provided with adjustment means and/or programming means for varying the intensity and/or the voltage and/or the modulation of the applied electric current. It is mentioned above that the fluid flow through the electric arc tends to blow the arc downstream along the flow direction. This has the effect of lengthening the arc, similar to moving the electrodes apart. In order to compensate for this elongation of the arc, it is necessary to increase the voltage at the terminals of the electrodes. Without going beyond the scope of the invention, it is possible to add servo-control means suitable for automatically varying the voltage and/or the current delivered by the generator as a function of the air flow rate.

Advantageously, the device is provided immediately behind the tool carrier 40 with a small voltage-boosting transformer 60, as schematically shown in FIG. 3. Given the frequencies used, i.e. several tens of kilohertz to several megahertz, such a transformer can be very small and, in accordance with the invention, it is important to limit the length of the path followed by high tension current. In accordance with an important characteristic of the invention, the transformer 60 is incorporated in a scalpel handle. The voltages used run from several hundreds of volts to several thousands of volts, depending on the difficulty of striking an arc, with said difficulty itself being a function of the electrodes (their shape and separation), and of the applied fluid(s) and of the surface of the substance to be treated. For example, the transformer may have a step-up ratio of four, and it may be fed with high frequency at 220 volts. The intensity of the electric current is limited by electrode lifetime or by the rate at which they are consumed.

It is practically indispensable to have the transformer incorporated in the moving portion of the device. If the transformer is at a distance from the scalpel, there is loss in the cable so that too little power or energy arrives at the electrodes. Further, unless additional bulky installation is used, there would be a danger of burning in the proximity of the wire. So long as a high magnetic field around the transformer is acceptable, the size of the transformer may be reduced by the transformer being constituted by a cylindrical rod core surrounded by its windings. This drawback does not exist if the magnetic circuit is closed (the windings are wound on a torus and the magnetic circuit is closed) but in that case the transformer is larger. In any event, the frequencies used are such that the dimensions of the transformer remain small.

The fluid(s) may pass through the transformer in order to cool it.

In dental or medical applications, at least, high or medium frequency is necessary in order to avoid any risk of electrocution. Pulse feed is also possible.

In order to strike the electric arc, it may be necessary in addition to conventionally moving the electrodes closer together, to act by adding a suitably conductive starting fluid such as a striking mist. It is also possible to strike the arc by applying a voltage peak, e.g. by means of a piezoelectric ceramic, however this is not entirely advisable in medical or dental applications.

Illumination means may also be added to the device, for example an electric lightbulb fitted with a light pipe may be provided in order to facilitate pre- and post-operative manual guidance, given the need to provide eye protection.

In accordance with the invention, the device may comprise a control box enabling all of the adjustments necessary for proper operation of the device to be centralized. Such a box should provide means, in particular, for adjusting:

the gas flow rate;
the water flow rate;
the electrical voltage;
the brightness of the light, which light may be cold light conveyed by a light pipe of the optical fiber type, for example;
the modulation of the electric current (rate, frequency); and
where applicable, adjustments relating to pulses (pulse duration, relaxation time, etc. . . .). In this context, the term "pulses" designates the short periods of time during which electric arcs are produced.

In an advantageous embodiment of the invention, a control system associated with a chamber inside the handle can be used to alternate the fluid applied to the lumen of at least one of the electrode-carriers. For example to alternate between applying a fluid appropriate to operating periods and a fluid which is particularly heat absorbent, e.g. water, during rest periods. Such control system provides an adjustable program of electric current and fluid flow in order to satisfy operating requirements.

In order to add material, one or more coated electrodes may be provided, or a wire of material to be added may be placed in the vicinity of the electrodes for the same purpose.

It may be necessary to provide additional means for exciting the plasma, which means may be electrical or chemical. For electrical excitation, D.C. may be superposed on high frequency A.C., even in dental or medical applications providing the total current remains below a danger threshold. As for chemical excitation, various different fluids may serve for cooling before an exothermal reaction takes place near the point of application.

During discontinuous or pulse operation, the "off" periods may be used for cooling the object both before and/or after the action of the plasma. This cooling may take place, in particular, using the same ducts or nozzles as those described, with the flow lines of the liquid and/or gas (charged or not charged) optionally serving on restarting as means for enhancing arc striking in order to initiate the plasma.

There are several possible variants of the device in accordance with the invention, in particular concerning symmetrical electrodes:

devices having solid convergent electrodes for dental, medical, and industrial applications: the arc which appears between the closest portions of the electrodes is blown by a fluid, e.g. air, which projects it. The electrodes may optionally be moved closer together for striking;

devices having hollow convergent electrodes for dental, medical, and industrial applications: the electrodes may be cooled internally by means of a fluid flowing in the hollow interior and serving to produce the plasma, instead of or in addition to the cooling provided by one or more nozzles projecting an optionally charged fluid such as an aerosol (including a solid or liquid dispersed phase). The electrodes may optionally be moved closed to one another for striking;

devices having hollow gas-blowing electrode-carriers together with consumable electrodes for dental, medical, or industrial applications: this is the example shown in FIG. 3 where the convergent electrode-carriers contain consumable wire electrodes having physical and/or chemical action. These electrodes are of slightly smaller diameter than the lumen of the electrode-carriers, thereby enabling the cooling fluid(s) participating in plasma production to pass therealong, which fluids may optionally be suitable for reacting with the object being treated or with one another. The electrodes may optionally be brought together for striking the arc. The consumable wire extends, if necessary, upstream from the electrode-carriers in order to provide a reserve supply. An automatic or manual electrode-advancing system may be provided. The, or each, fluid may be conveyed via one or more ducts which are concentric with the electrode-carriers, and one or more nozzles may be added or substituted for projecting one or more of the fluids which may optionally be charged (with a solid or liquid dispersed phase); and multiple electrode devices for dental, medical, and industrial applications: apparatuses having n electrodes (where n is an integar) fed with single phase electricity or with polyphase electricity giving rise to an alternating or a rotating plasma which may be blown and/or guided by D.C., A.C., or pulsed electrical or magnetic fields.

For devices having a symmetrical electrode, the following configurations are possible within the scope of the present invention:

a plane configuration for dental, medical, and industrial applications: a first electrode is placed ahead of a second electrode which is slightly set back and bent or inclined towards the first and the electrodes may optionally be fed asymmetrically and/or may be subjected to different fluid flows. This configuration enhances the activity of one of the electrodes relative to the other. There may be a plurality of electrodes similar to the second disposed around the first electrode. The electrodes may eventually be moved towards one another for striking an arc. The gas-conveying electrode-carrying ducts may optionally be replaced by one or more nozzles;

a bulk configuration for dental, medical, and industrial applications: a first linear electrode is surrounded at one end by a second, ring-shaped electrode, and the electrodes may optionally be powered asymmetrically and may be fed with asymmetric fluid flows in order to circumscribe the action by virtue of the ring-shape of the second electrode, which electrode may also be in the form of a metal plate having a hole therein. The electrodes may optionally be moved towards one another for striking an arc. Here too, the gas-conveying electrode-carriers may be replaced by one or more nozzles.

There are numerous possible applications for such devices:

in dental surgery it is possible to treat enamel and dentine in a manner which is comparable to using a laser. It is also possible to use the light emitted by the production of the plasma for activating photopolymerization of certain substances, in particular certain resins, which are used for filling holes drilled in teeth during dental care or for making dental protheses, since the color temperatures of the emitted light are suitable for this application, providing filters are used, which filters may be cooled by the fluid(s) emitted;

in medical applications the device may be used for tissue exeresis; the miniaturization of the apparatus makes endoscopic type utilization possible for operating inside a living organism; the capacitive effect of the system can then be used to make an oscillating circuit which is tuned so as to reduce the losses resulting from the need to operate at a distance from the transformer;

numerous developments are possible in other fields, in particular for etching, cutting, welding, or refilling operations, in the treatment of composite materials, etc. . . .

Further, returning to the example of FIG. 3, the tool carrier 40 may be suitable for feeding tools other than the electrode-carrier assembly 41. It has been mentioned that the light emitted by the plasma can be used for activating photopolymerization reactions. The FIG. 3 device may also be used for performing conventional tissue electrode sections on a monopolar or a bipolar basis, using one or two electrodes. The capacitive effect of the transformer makes it possible to use the apparatus as a monoactive bipolar electrical scalpel with the two high frequency wires of the cord being fed from the same terminal, with the other terminal serving, optionally, as an unspecialized electrode placed in the vicinity of the patient. The plasma micro-blowtorch or scalpel configuration could be referred to, in the terms used in electrode surgery, as a very high temperature mesioactive biactive bipolar configuration.

The device is thus versatile since it provides the functions of three different implements in a single implement (plasma scalpel, electric scalpel, light source for photopolymerization).

We claim:

1. A device of the plasma scalpel type, comprising: a scalpel handle having at least two spaced-apart electrodes subjected to differences in electrical potential such that electric arcs occur therebetween, and means for producing at least one fluid flow passing through a region of space where said electric arcs occur, wherein said potential differences are alternating differences at medium or high frequency, wherein the ends of said electrodes are substantially filiform or pointed and form an acute angle therebetween, and wherein a voltage step-up transformer is incorporated in said handle to deliver said alternating potential differences, said fluid flows arriving from inside said angle or along at least one of said electrodes.

2. A device according to claim 1, wherein each of said electrodes is constituted by a wire of electrically conductive material, and is placed in an electrode-carrying duct whose inside diameter is slightly greater than the diameter of the electrode, with the end of the electrode projecting beyond the end of the duct, and wherein said fluids are conveyed by said electrode-carrying ducts.

3. A device according to claim 2, wherein said electrode-carrying ducts and/or said electrodes are consumable, interchangable, and replaceable.

4. A device according to claim 2, wherein the electrode-carrying ducts communicate with a chamber suitable for being put under pressure by at least one of said fluids under the control of closure means provided between said chamber and at least one fluid admission tube.

5. A device according to claim 1, wherein means are provided for adjusting or programming the electrical potential differences and the relaxation times between the periods during which said potential differences are applied, said means also serving to adjust the durations of said periods.

6. A device according to claim 1 wherein means are provided for adjusting the fluid flow rates.

7. A device according to claim 1, wherein the two electrodes form plane curves each defining a plane, said planes forming an angle therebetween suitable for enabling the operating field to be observed from inside said angle which is preferably acute, thereby enabling said operation to take place along an observation axis which is substantially perpendicular to the surface of the object on which work is being performed.

8. A device according to claim 1, wherein the electrodes are hollow and convey said fluids.

9. A device according to claim 1, wherein means are provided for conveying water to the vicinity of the ends of the electrodes.

10. A device according to claim 9, wherein each of said electrodes is constituted by a wire of electrically conductive material, and is placed in an electrode-carrying duct whose inside diameter is slightly greater than the diameter of the electrode, with the end of the electrode projecting beyond the end of the duct, wherein said fluids are conveyed by said electrode-carrying ducts and wherein the water is conveyed via at least one of the electrode-carrier ducts.

11. A device according to claim 4, wherein said closure means comprise a rigid sleeve having at least two fluid admission tubes which are highly deformable inside the sleeve so that a high pressure in one of the tubes closes the other tube(s) by compression against the inside walls of said rigid sleeve.

* * * * *